(12) United States Patent
Inman (10) Patent No.: US 6,435,871 B1
(45) Date of Patent: Aug. 20, 2002

(54) ORTHODONTIC APPLIANCE AND METHOD (76) Inventor: Donal P. Inman, 4911 NW. 101st Ave., Coral Springs, FL (US) 33076

( * ) Notice: Subject to any disclaimer, the term of this patent is extended or adjusted under 35 U.S.C. 154(b) by 0 days.

(21) Appl. No.: 09/932,641

(22) Filed: Aug. 17, 2001

Related U.S. Application Data
(60) Provisional application No. 60/285,881, filed on Apr. 23, 2001.

(51) Int. Cl.[7] .................................................. A61C 7/00
(52) U.S. Cl. ............................................. 433/7; 433/21
(58) Field of Search ............................ 433/6, 7, 18, 21

(56) References Cited

U.S. PATENT DOCUMENTS

| | | | |
|---|---|---|---|
| 3,798,773 A | | 3/1974 | Northcutt |
| 4,413,978 A | * | 11/1983 | Kurz .............................. 433/6 |
| 4,551,095 A | | 11/1985 | Mason |
| 4,723,910 A | * | 2/1988 | Keller ........................... 433/7 |
| 5,022,855 A | | 6/1991 | Jeckel |
| 5,064,370 A | * | 11/1991 | Jones .......................... 433/18 |
| 5,167,499 A | | 12/1992 | Arndt et al. |
| 5,352,116 A | | 10/1994 | West |
| 5,645,422 A | | 7/1997 | Williams |
| 5,769,631 A | * | 6/1998 | Williams ........................ 433/7 |
| 5,785,520 A | * | 7/1998 | Carano et al. ................. 433/7 |
| 5,829,970 A | * | 11/1998 | Yousefian ...................... 433/7 |
| 5,967,774 A | | 10/1999 | Teramoto |
| 6,033,217 A | | 3/2000 | Shirasuka |
| 6,113,390 A | | 9/2000 | Sirney et al. |
| 6,162,051 A | | 12/2000 | Brehm et al. |
| 6,241,517 B1 | | 6/2001 | Williams |

* cited by examiner

Primary Examiner—Cary E. O'Connor
(74) Attorney, Agent, or Firm—Gold & Rizvi, P.A.; Glenn E. Gold; H. John Rizvi (57) ABSTRACT An orthodontic appliance (10) for treating anterior teeth of a patient includes a support structure (12, 14) having labial and lingual components for applying opposed forces to a set of targeted teeth. The labial component includes a labial arch (20) having an encapsulated (26) labial bow (34) and distal extending portions (27) extending through sleeves (18) attached to clasps (16), and compressed springs (25) disposed between hooked ends (22) of the wire and the sleeve ends (19). The lingual component includes a lingual rod (30) having a mushroom-shaped center (34) encapsulated in a hard acrylic body (35) and distal extending portions extending through sleeves (36). Compressed springs (40) are disposed between the sleeve end (38) and the hard body.

20 Claims, 8 Drawing Sheets

ORTHODONTIC APPLIANCE AND METHOD

CROSS REFERENCE TO RELATED APPLICATIONS

This application is co-pending with and claims the priority of provisional patent application serial No. 60/285,881, filed Apr. 23, 2001.

BACKGROUND OF THE INVENTION

1. Field of the Invention

The present invention relates generally to orthodontic appliances and treatments, and more particularly to appliances and treatments for correction of problems specific to the anterior teeth.

2. Description of the Prior Art

Orthodontists and dental researchers are constantly searching for new and improved appliances and associated treatments for correcting problems related to the anterior teeth, including, for example, cross-bites, overcrowding, rotated teeth, and splayed or flared teeth. Some known orthodontic appliances for treating such problems include both labial and lingual components for applying corrective forces to the respective labial and lingual surfaces of the anterior teeth identified for treatment. Although many such devices are effective for accomplishing the desired correction, they leave much room for improvement.

Figure 1:
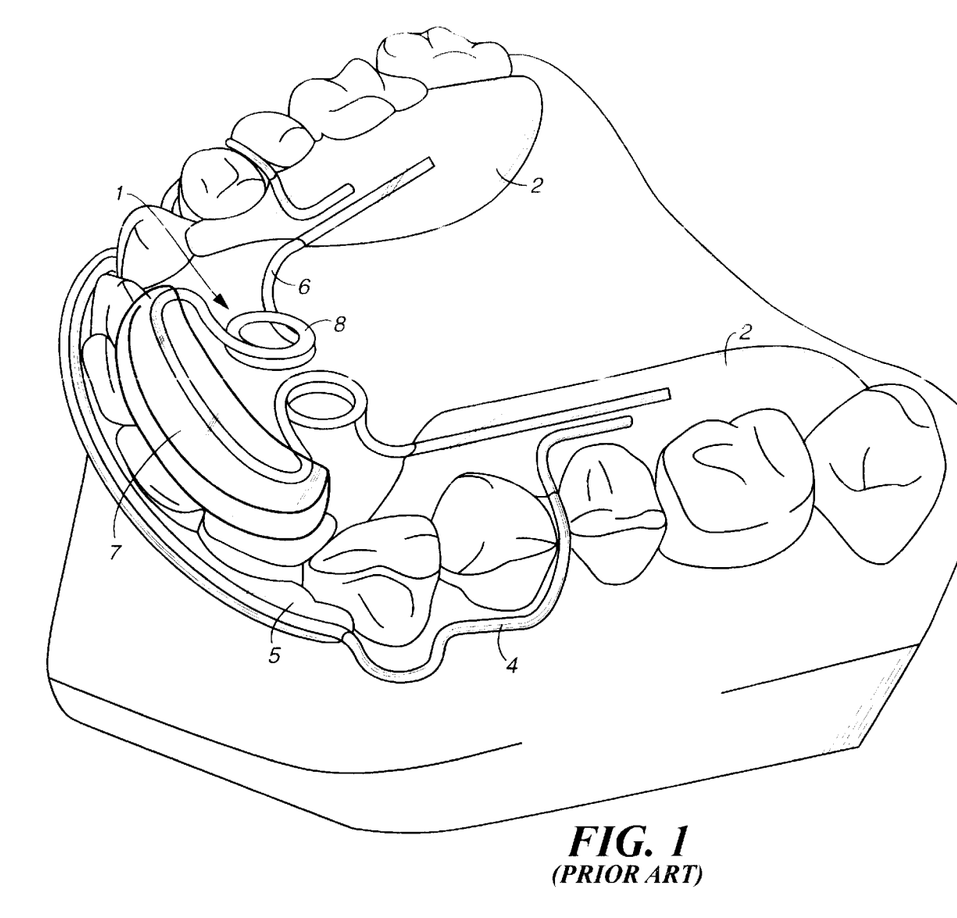
FIG. 1 is perspective view of an exemplary prior art anterior appliance.

The disadvantages and limitations associated with existing appliances are in large measure related to their design and construction. In particular, most devices incorporate fixed, generally immovable labial and lingual components. The device illustrated in FIG. 1 is exemplary of such prior art devices. The exemplary device, shown generally as reference numeral 1, includes a one-piece labial wire 4 and a one-piece lingual wire 6, each having distal ends fixed in one or more acrylic bodies 2. Anterior portions of the labial 4 and lingual 6 wires are each encapsulated within conventional teeth engaging acrylic bodies, 5 and 7, respectively.

In general, orthodontic appliances must be periodically adjusted to reestablish the desired forces on the teeth targeted for treatment. These adjustments are primarily accomplished by bending the labial and lingual wires. For instance, in order to make adjustments to the labial portion of the aforementioned prior art device 1, wire 4 must be manually bent using an adjustment tool. Similarly, adjustment of the lingual portion of the device requires manual manipulation of the integral helical portions 8. Commonly, such adjustments actually involve making multiple fine-tuning adjustments, requiring the orthodontist to repeatedly adjust and reseat the device in the patient's mouth until the overall desired adjustment is achieved. To further complicate matters, the appliances are prone to ejection from the patient's mouth, especially during seating, if the adjustments are not made with precision. Consequently, the adjustment of prior art devices typically requires the expertise of a skilled and experienced orthodontist or technician.

The difficulties associated with adjusting the prior art appliances are a direct result of the limited flexibility, or play, inherent in their design. Another drawback of the fixed labial and lingual wire design is that the desired force of the labial and lingual components against the teeth (i.e., following an adjustment) steadily decreases as the teeth are repositioned in response to the force. Consequently, adjustments of conventional appliances are required at relatively short time intervals, requiring quite frequent patient visits. Furthermore, the overall treatment time is increased due to the inability to maintain a constant desired force against the teeth between adjustments.

Accordingly, there is a well-recognized need within the orthodontic community for an improved anterior appliance overcoming the aforementioned drawbacks and limitations of the prior art.

SUMMARY OF THE INVENTION

It is an object of the present invention to provide an orthodontic appliance and method for treating various conditions related to the anterior teeth of a patient, including cross-bites, overcrowding, rotated teeth, and splayed or flared teeth.

It is another object of the present invention to provide such an appliance incorporating labial and lingual components acting in generally opposed directions, and in unison, against the respective labial and lingual surfaces of a set of targeted anterior teeth.

It is another object of the present invention to provide such an appliance wherein the design of the labial and lingual components enable the application of a relatively continuous force against the targeted teeth between scheduled treatments, with minimal reduction in applied force.

It is another object of the present invention to provide such an appliance wherein the labial and lingual components incorporate a spring-loaded biasing means having improved flexibility. Furthermore, the improved flexibility should facilitate adjustment of the appliance as well as appliance seating in a patient's mouth, and reduce the likelihood that the appliance will become inadvertently disengaged from the patient's mouth during and after seating.

It is another object of the present invention to provide such an appliance wherein adjustments to the appliance can be made without requiring bending or manipulation of the labial and lingual wires.

It a another object of the present invention to provide such an appliance wherein the improved flexibility and adjustability of the device are sufficient to enable less skilled, less experienced dental professionals to effectively incorporate the device into their practice as a treatment.

These and other objects of the invention are not intended to be limiting and are described in further detail hereinbelow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

DETAILED DESCRIPTION OF THE PREFERRED EMBODIMENTS

Figure 2:
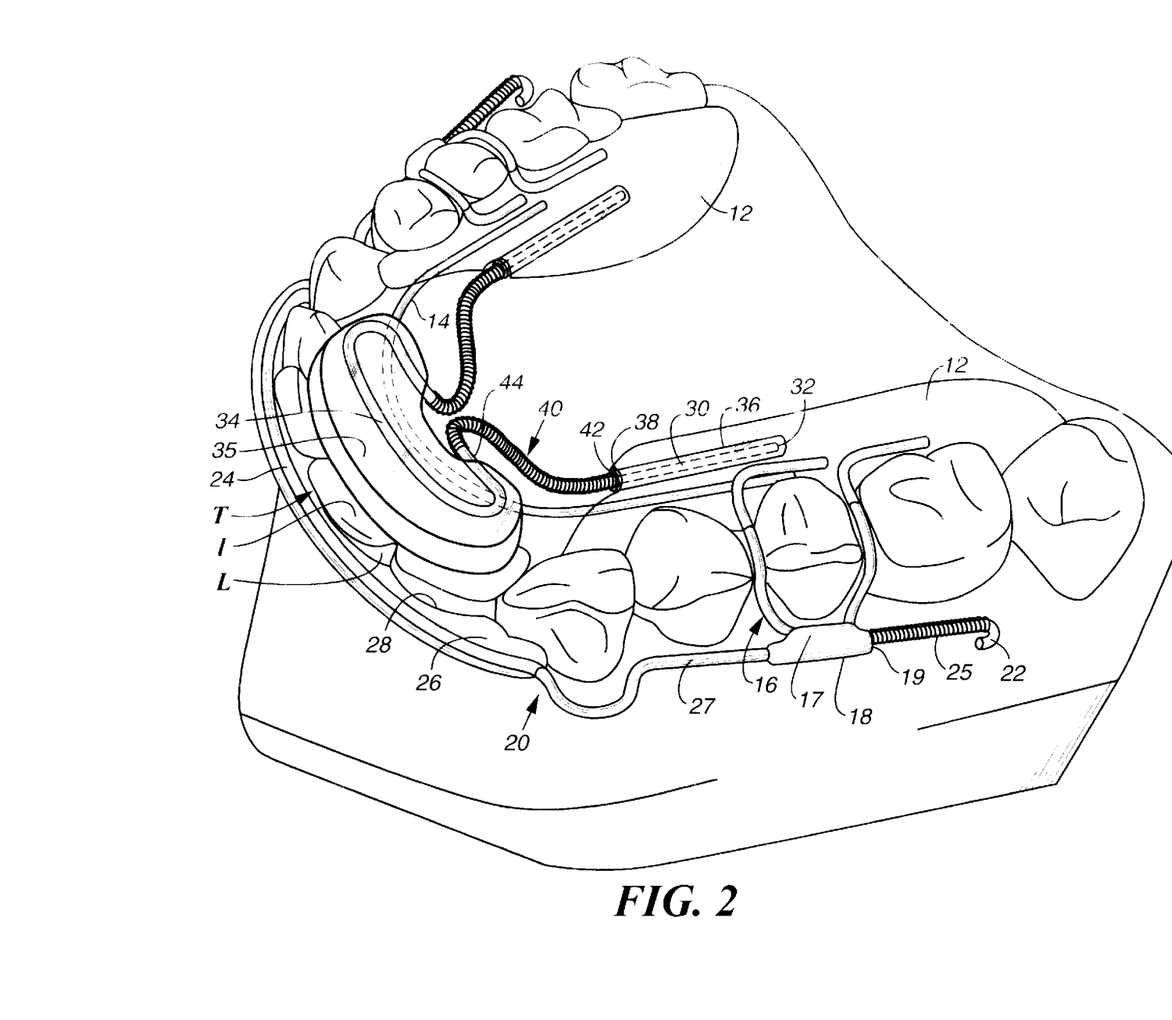
FIG. 2 is a perspective view of an orthodontic appliance in the upper mouth of a patient, in accordance with a preferred embodiment of the present invention.
Figure 3:
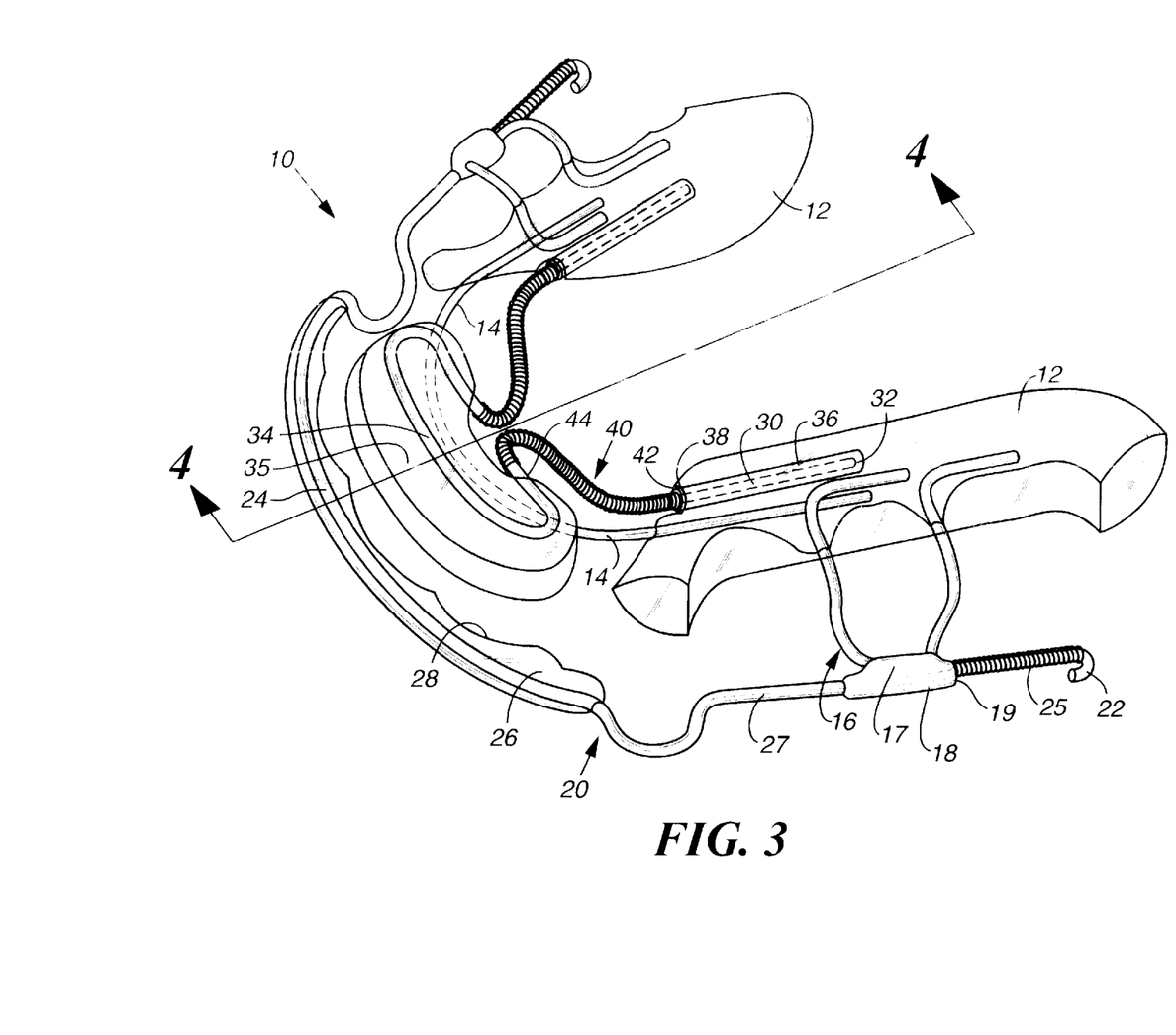
FIG. 3 is a perspective view of the appliance depicted in FIG. 2 isolated from the patient's mouth.
Figure 4:
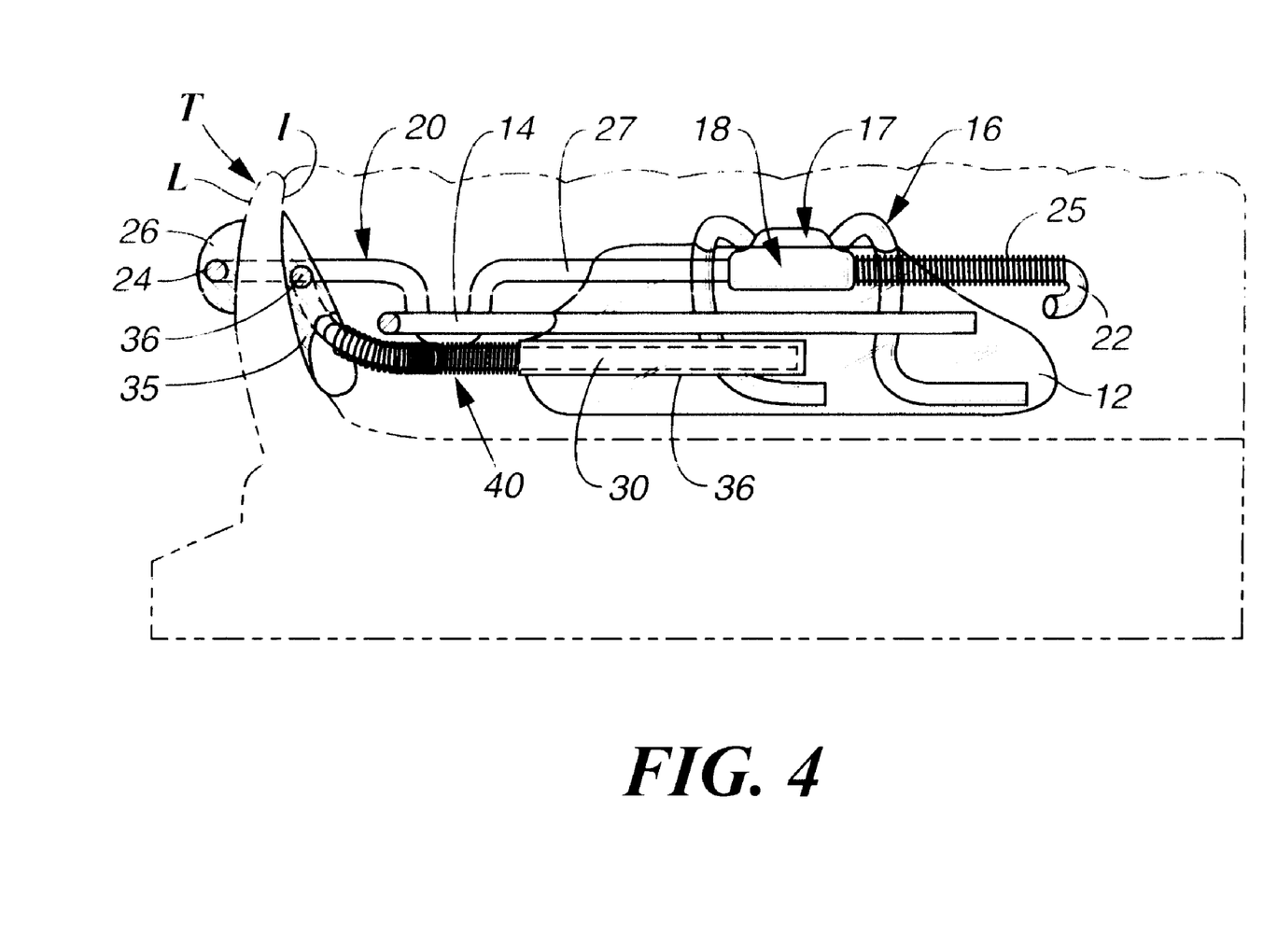
FIG. 4 is a cross-sectional view taken along line 4—4 of FIG. 3.

Referring now particularly to FIGS. 2–4 of the drawings, an orthodontic appliance for treating the anterior teeth of a patient is illustrated in accordance with a preferred embodiment of the invention. The appliance, shown generally as reference numeral 10, is constructed about a main support structure including a main support arch wire 14 having distal extending ends encapsulated within a pair of laterally opposed hardened acrylic bodies 12. As will be apparent to those skilled in the art of orthodontics, where the appliance is intended for use in the upper jaw of a patient, the acrylic bodies 14 could be joined by a palate portion (not shown). In that case, support wire 14 would not be necessary. Furthermore, although FIG. 2 illustrates the appliance 10 seated within the upper jaw of a mouth, the appliance functions in a similar manner in the lower jaw.

A pair of attachment members 16, such as Adams clasps and the like, are constructed for temporary engagement with selected rear teeth of the jaw of the patient. Preferably, the clasps 16 are constructed for engagement with the second bicuspids. Alternatively, in cases where the first bicuspids have been extracted, the clasps 16 are preferably fitted for engagement with the first molars. Each clasp 16 is fixedly attached to one of the lateral acrylic bodies 12 preferably by encapsulating portions of the lingual side of the clasp within the acrylic during fabrication of the appliance 10. Each clasp 16 has a stainless steel sleeve 18, such as standard 0.040 inch stainless tubing, attached to its labial side by a solder joint 17.

A labial rod, such as a standard 0.030 inch spring hard wire, shown generally as reference numeral 20, is shaped in the form of a conventional labial arch 24 having distally extending sections or lengths 27 each terminating at a bent or hooked end 22. Alternatively, auxiliary stop mechanisms, such as crimped members and the like, can be used in lieu of hooked ends 22. A labial body portion 26, such as a hardened acrylic, is carried by labial bow 24. Preferably, the labial body portion 26 has an inner surface 28 having an impression of the labial surfaces of the selected anterior teeth, T, when the teeth are in an ideal, or desired post-treatment position and orientation.

The distal extending sections 27 of the labial rod 20 are slidably received in and extend through and beyond the sleeves 18. A compressed member, such as coil spring 25, is journaled about each of the distal portions of the labial rod 20 such that the member 25 is compressed between the hooked end 22 and the rear end 19 of sleeve 18. In this manner, the compressive force of the spring against the hooked end 22 urges the labial rod in a posterior direction. Accordingly, the magnitude of the force applied by the labial component of the appliance can be easily adjusted by simply incorporating a spring having particular desired compressive properties and/or by modifying the length of the spring. Some examples of coil spring that work well with the appliance include stainless steel coil, elgiloy coil and NiTi coil, to name just a few.

A lingual rod member, such as conventional 0.030 inch spring hard wire, shown generally as reference numeral 30, has a length generally defined by a midsection 34 bent into the general shape of a mushroom, and a pair of generally parallel, distal extending sections terminating at ends 32. A lingual body 35 carried on the midsection 34 of rod 30, is provided for at least partially engaging and directly applying a force to the lingual surfaces, I, of the targeted anterior teeth T. Preferably, the lingual body portion 26 has a lingual contact surface (not shown) comprising an impression of the lingual surfaces I of the targeted teeth T with the targeted teeth in the ideal or desired post-treatment position and orientation. Although lingual rod 30 is illustrated as a unitary member, it will be appreciated by those skilled in the art that a pair of symmetric lingual rod members could be substituted without departing from the scope of the invention.

A second pair of sleeve members 36, such as conventional 0.040 inch stainless steel tubing, are provided substantially encapsulated within the opposed lateral bodies 12. Each sleeve 36 includes a forward end 38 having an opening sized and shaped for slidably receiving the distal extending portions of lingual rod 30.

The distal extending portions of lingual rod 30 are slidably received in and extend into the sleeves 36. A compressed member, such as coil spring 40, is journaled about a segment of the distal extending portions of the lingual rod 30 with end 42 of spring 40 contacting end 38 of sleeve 36, and end 44 of spring 40 contacting body 35. In this manner, the spring is maintained in a compressed state between the sleeve 36 and the lingual body 35, thereby urging the lingual rod 30 and body 35 in an anterior, or forward, direction. Accordingly, the magnitude of the force applied by the lingual component of the appliance can be easily adjusted by incorporating a spring having particular desired compressive properties and/or by modifying the length of the spring.

Figures 5, 6:
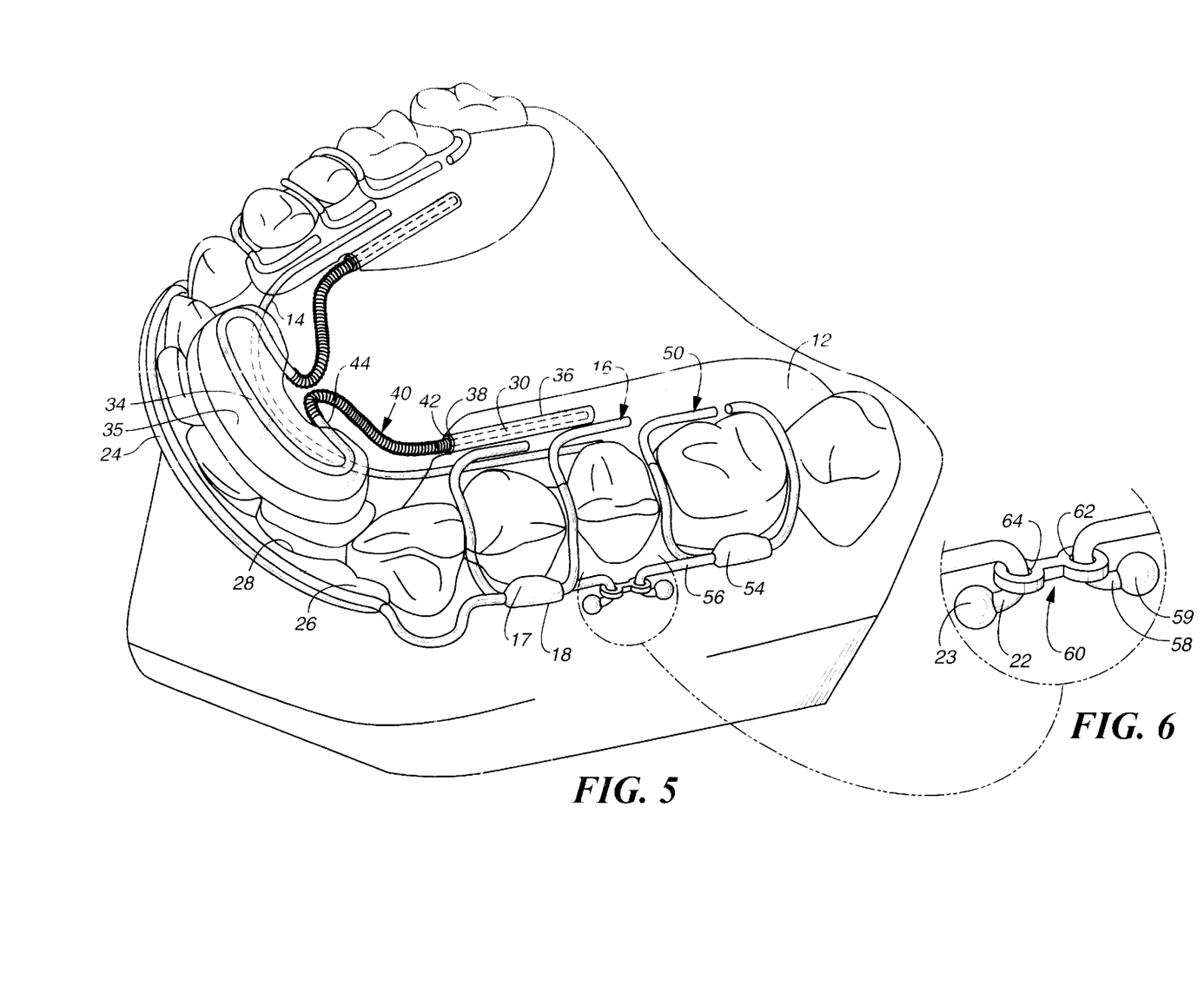
FIG. 5 is a perspective view of an orthodontic appliance incorporating elastic members 60 for providing the desired labial force, in accordance with an alternate embodiment of the present invention.
FIG. 6 is a magnified view of the elastic member 60 of FIG. 5.

Referring now to FIG. 5, in another embodiment of the present invention, a second pair of dental clasps 50 are provided for securely engaging a second set of laterally opposed rear teeth of the jaw posterior to the rear teeth engaged by the first pair of clasps 16. An anterior extending rod 56 having a hooked end 58 is attached to each clasp 50 by a solder joint 54. Preferably, mechanical stop mechanisms 23 and 59 are provided on hooked ends 22 and 58, respectively. A tension member is provided attached to the respective hook ends 22, 58 for maintaining a pulling force therebetween. Preferably, the tension member comprises an elastic band, such as that shown generally as reference numeral 60, having a pair of integral eyelets, 64 and 62, shaped and sized for attachment to the respective hook ends, 22 and 58. The pulling force created by the elastic member 60 urges the labial rod 20, and corresponding labial arch 24 and body 26, in a posterior direction for applying the desired force against the labial surfaces of the anterior teeth targeted for treatment. The desired force can be modified by incorporating bands having varying degrees of tension or, alternatively, by using bands of varying lengths. It will be appreciated that alternative means can be employed for providing the desired force, in lieu of the preferred elastic member 60. For example, conventional elastic bands work well, as do various inelastic members such as springs.

Figure 7:
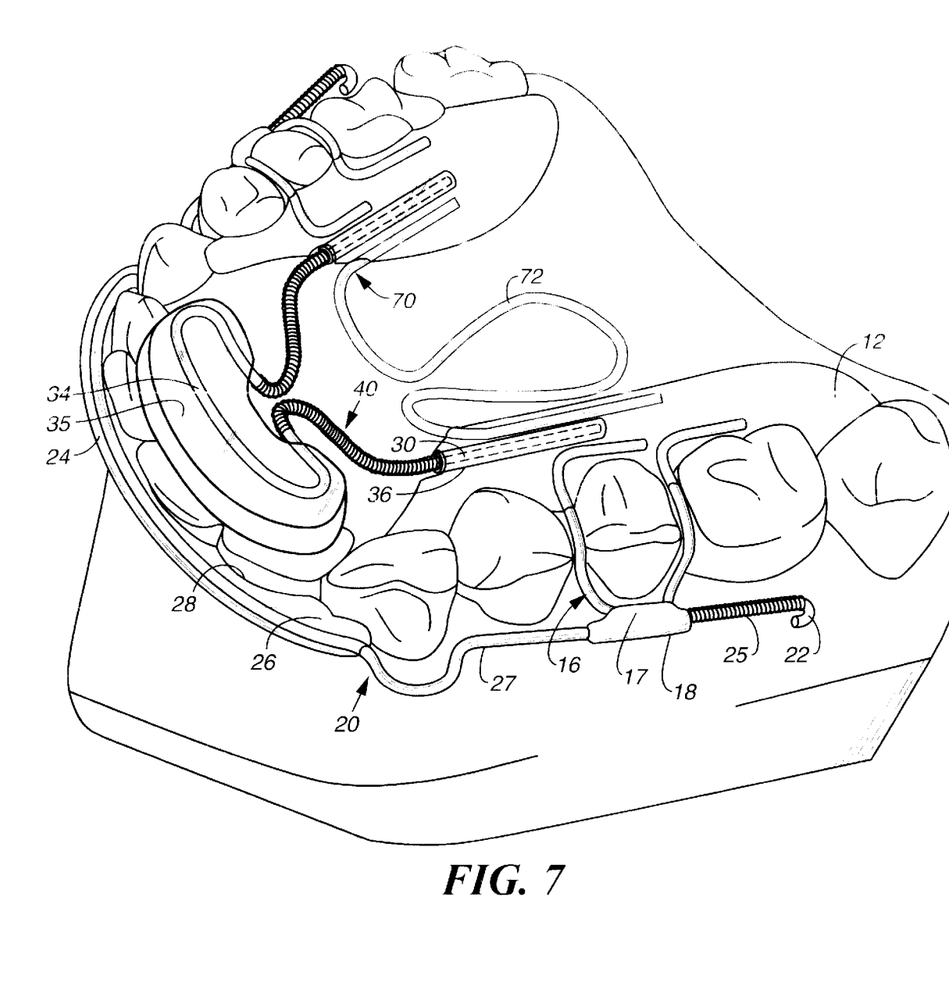
FIG. 7 is a perspective view of an orthodontic appliance incorporating an expansion arch 72, in accordance with another alternate embodiment of the invention.

Referring briefly to FIG. 7, in a further embodiment of the invention, an "M-shaped" preformed palatal expansion arch wire, shown generally as reference numeral 70, is provided having distal extending end portions encapsulated within laterally opposed acrylic bodies 12. The midsection 72 of the arch wire is generally centered with the midpoint of the palatal concavity and extends in a posterior direction.

Figure 8:
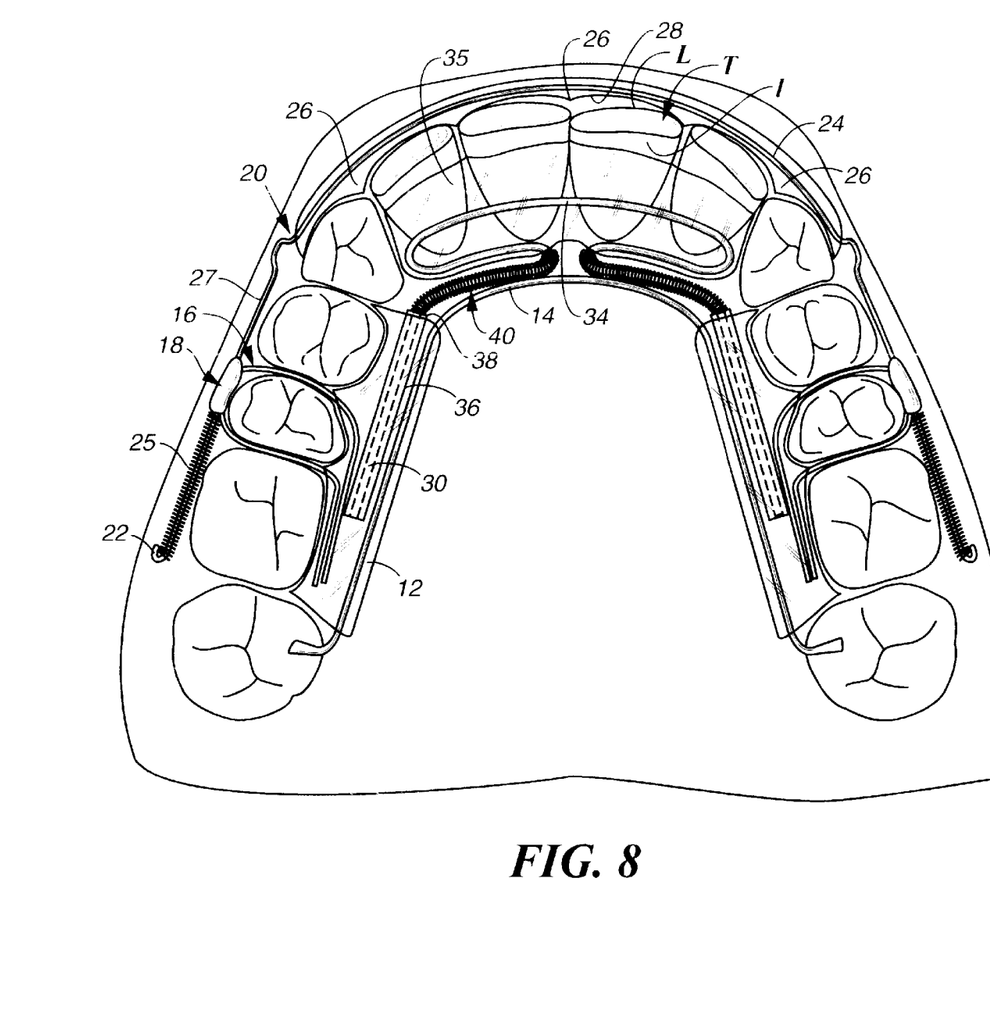
FIG. 8 is a top view of the appliance of the present invention seated in the lower mouth of a patient at the beginning of a treatment period.
Figure 9:
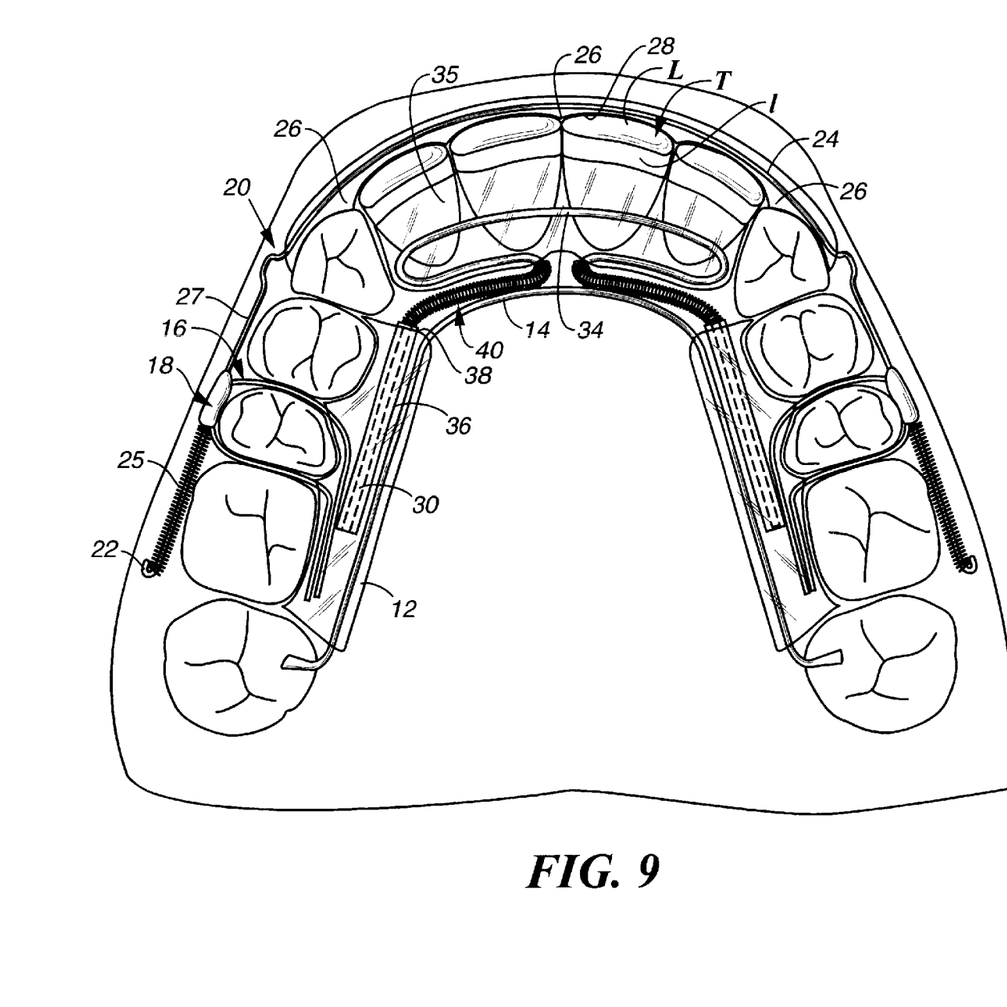
FIG. 9 is a top view of the appliance of the present invention seated in the lower mouth of a patient following a complete treatment.

Referring now specifically to FIGS. 8 and 9, use of the appliance for treating various anterior related conditions will now be described in more detail. Prior to fabricating the appliance, a dental cast of the patient's teeth in the appropriate jaw is created using a hardenable refractory material, as is well known in the art. The anterior teeth targeted for treatment are removed from the cast and then reset on the cast with wax in the desired post-treatment position and orientation. Subsequently, the appliance is fabricated using the "corrected" cast, with the labial and lingual components constructed such that teeth-contacting surfaces of the corresponding labial and lingual acrylic bodies, 26 and 35, respectively, are formed with an impression of the corresponding labial and lingual surfaces, L and I, in desired post-treatment alignment.

In FIG. 8 the appliance is illustrated seated in the mouth of a patient prior to treatment. As can be seen, surface 28 of the labial body 26 only contacts portions of the labial surfaces L of the targeted anterior teeth T. Similarly, the lingual contacting surface (not shown in FIG. 8) of the lingual body 35 only contacts portions of the lingual surfaces I of the targeted anterior teeth. During the course of treatment, the labial and lingual components of the appliance provide desired respective labial and lingual forces to the targeted teeth. Referring specifically to FIG. 9, following treatment, with the targeted anterior teeth in the desired position and orientation, the inner surface 28 of labial body 26 has substantially improved contact or engagement with the labial surfaces L of the targeted teeth. Similarly, the surface contact area of the lingual-facing surface of lingual body 35 and lingual surface I of the targeted teeth is maximized.

While the preferred embodiments of the invention have been illustrated and described, it will be clear that the invention is not limited to these embodiments only. Numerous modifications, changes, variations, substitutions and equivalents will be apparent to those skilled in the art without departing from the spirit and scope of the present invention as described in the claims.

What is claimed is:

1. Apparatus for the orthodontic treatment of one or more anterior teeth in a jaw of a patient, comprising:
   a support structure including laterally opposed body portions;
   a pair of attachment members adapted for securely engaging selected rear teeth of one jaw of a patient, each attachment member fixedly attached to one of the laterally opposed body portions of the support structure;
   a first pair of sleeve members each attached to the labial side of one of said attachment members;
   a labial rod member having a form generally defined by a medially positioned arch separating a pair of a straight distal extending sections, the distal extending sections received within and extending distally through said first pair of sleeve members, each of said distal extending portions having an end;
   first biasing means positioned between the ends of the distal extending sections and posterior ends of the first pair of sleeve members, the first biasing means urging the labial arch in a posterior direction;
   a second pair of sleeve members attached to the laterally opposed body portions of the support structure;
   a lingual rod member having a length generally defined by a bent medial section separating a pair of distal extending sections, the distal extending sections received within the second pair of sleeve members, the medial section carrying a hardened body sized and shaped for comfortably engaging the lingual side of the anterior teeth; and
   second biasing means positioned between the anterior ends of the second pair of sleeve members and the outer surface of the hardened body carried by the medial section of the lingual rod member, the second biasing means urging the hardened body in an anterior direction.

2. An apparatus as recited in claim 1, further comprising a support arch wire having distal extending ends encapsulated within said laterally opposed body portions.

3. An apparatus as recited in claim 1, wherein the appliance is particularly adapted for treating anterior teeth in the upper jaw of a patient, and wherein said laterally opposed hardened body portions are joined by a palate portion.

4. An apparatus as recited in claim 1, wherein said attachment members comprise dental clasps.

5. An apparatus as recited in claim 4, wherein each dental clasp is partially encapsulated within one of the laterally opposed body portions of the support structure.

6. An apparatus as recited in claim 1, wherein the first pair of sleeve members are each spot welded to the labial side of one of the attachment members.

7. An apparatus as recited in claim 1, further comprising a labial body portion carried by the medially positioned arch of said labial rod member.

8. An apparatus as recited in claim 1, wherein the ends of the distal extending portions of the labial rod member each have a stop mechanism.

9. An apparatus as recited in claim 8, wherein the stop mechanism further comprises a hooked end portion of the labial rod member.

10. An apparatus as recited in claim 1, wherein the first biasing means positioned between the ends of the distal extending sections and posterior ends of the first pair of sleeve members further comprise compressed members.

11. An apparatus as recited in claim 10, wherein the compressed members further comprise spring coils journaled about the respective distal extending sections of the labial rod member, each spring coil compressed between the end of one distal extending section and an end of one of the first pair of sleeve members.

12. An apparatus as recited in claim 1, wherein the second pair of sleeve members are substantially encapsulated within the respective laterally opposed body portions of the support structure.

13. An apparatus as recited in claim 1, wherein the bent medial section of said lingual rod member is mushroom-shaped.

14. An apparatus as recited in claim 1, wherein the second biasing means positioned between the anterior ends of the second pair of sleeve members and the outer surface of the hardened body carried by the medial section of the lingual rod member further comprise compressed members.

15. An apparatus as recited in claim 14, wherein the compressed members further comprise spring coils journaled about the respective distal extending sections of the lingual rod member, each spring coil compressed between an anterior end of one of the second sleeve members and the outer surface of the hardened body carried by the medial section of the lingual rod.

16. An apparatus as recited in claim 1, further comprising a palatal expansion arch interposed between said laterally opposed bodies and having ends encapsulated therein.

17. Apparatus for the orthodontic treatment of one or more anterior teeth in a jaw of a patient, comprising:

a support structure including laterally opposed hardened body portions;

a first pair of attachment members adapted for securely engaging a first pair of laterally opposed rear teeth of one jaw of a patient, each attachment member fixedly attached to an adjacent one of the laterally opposed body portions of the support structure;

a first pair of sleeve members each attached to the labial side of one of said first pair of attachment members;

a second pair of attachment members adapted for securely engaging a second pair of laterally opposed rear teeth of said jaw posterior to the first pair of teeth, each of the second attachment members fixedly attached to an adjacent one of the laterally opposed body portions of the support structure and each including an anterior extending member having a hooked end;

a labial rod member having a form generally defined by a medially positioned arch separating a pair of a straight distal extending sections, the distal extending sections received within and extending distally through said first pair of sleeve members, each of said distal extending portions having a hooked end;

a pair of biasing members each attaching a hooked end of one of the first attachment members and a hooked end of an adjacent second attachment member, the biasing members urging the labial arch in a posterior direction;

a second pair of sleeve members attached to the laterally opposed body portions of the support structure;

a lingual rod member having a length generally defined by a bent medial section separating a pair of distal extending sections, the distal extending sections received within the second pair of sleeve members, the medial section carrying an acrylic body sized and shaped for comfortably engaging the lingual side of the anterior teeth; and a pair of compressed members positioned between the anterior ends of the second pair of sleeve members and the outer surface of the hardened body carried by the medial section of the lingual rod member, the compressed members urging the lingual rod member and the hardened body carried thereon in an anterior direction.

18. An apparatus as recited in claim 17, wherein the biasing members are elastic.

19. An apparatus as recited in claim 18, wherein said elastic member further comprises an elongated body having integral eyelets provided at its ends.

20. An apparatus as recited in claim 17, wherein the compressed members further comprise coil spring members journaled about the respective distal extending sections of the lingual rod member, each spring coil compressed between an anterior end of one of the second sleeve members and the outer surface of the hardened body carried on the bent medial section of the lingual rod.

* * * * *